United States Patent
Assmann et al.

[11] Patent Number: 6,043,377
[45] Date of Patent: Mar. 28, 2000

[54] IMIDAZOLE COMPOUNDS

[75] Inventors: Lutz Assmann, Peter-Ording; Hans-Ludwig Elbe, Wuppertal; Ralf Tiemann; Markus Heil, both of Leverkusen; Klaus Stenzel, Düsseldorf, all of Germany

[73] Assignee: Bayer Aktiengesellschaft, Leverkusen, Germany

[21] Appl. No.: 09/202,090

[22] PCT Filed: May 30, 1997

[86] PCT No.: PCT/EP97/02830

§ 371 Date: Dec. 8, 1998

§ 102(e) Date: Dec. 8, 1998

[87] PCT Pub. No.: WO97/47620

PCT Pub. Date: Dec. 18, 1997

[30] Foreign Application Priority Data

Jun. 11, 1996 [DE] Germany .............. 196 23 207

[51] Int. Cl.⁷ .............. C07D 413/12; C07D 401/12; A01N 43/80; A01N 43/58
[52] U.S. Cl. .............. 548/243; 514/316.4; 514/325.1; 548/111
[58] Field of Search .................. 548/111, 243, 548/316.4, 325.1

[56] References Cited

U.S. PATENT DOCUMENTS

| | | | |
|---|---|---|---|
| 3,519,639 | 7/1970 | Budde et al. | 260/309 |
| 3,595,873 | 7/1971 | Budde et al. | 260/309 |
| 4,179,277 | 12/1979 | Beck et al. | 71/92 |
| 4,369,186 | 1/1983 | Beck et al. | 424/273 R |
| 4,734,427 | 3/1988 | Riebel et al. | 514/398 |
| 4,804,673 | 2/1989 | Saito et al. | 514/398 |
| 4,995,898 | 2/1991 | Nasu et al. | 71/90 |
| 5,045,557 | 9/1991 | Buss et al. | 514/398 |
| 5,096,915 | 3/1992 | Parsons et al. | 514/398 |

FOREIGN PATENT DOCUMENTS

| | | | |
|---|---|---|---|
| 0 044 394 | 1/1982 | European Pat. Off. | |
| WO 92/07835 | 5/1992 | WIPO | 548/111 |
| WO 95/17390 | 6/1995 | WIPO | |

OTHER PUBLICATIONS

Patent Abstracts of Japan, vol. 11, No. 369 (C–461) Dec. 2, 1987 & JP 62 142164 A (Ishihara Sangyo Kaisha Ltd.) Jun. 25, 1987.

Patent Abstracts of Japan, vol. 18, No. 19(C–1152), Jan. 13, 1994 & JP 05 255269 A (Agro Kanesho Co. Ltd.) Oct. 5, 1993.

Chem. Ber. (month unavailable) 1877, vol. 10, 1365–1375 (see p. 1370), Wyss.

J. Heterocycl. Chem. (Sep. 1967) vol. 4, 399–402, Lutz et al.

Chem. Ber. (month unavailable) 1976, vol. 109, 1625–1637, Buchel et al.

J. Chem. Soc. (month unavailable) 1910, vol. 97, 1814–1832–(see p. 1824), Pyman.

J. Chem. Soc. Parkin Trans., I, (month unavailable) 1989, pp. 95–99, Palmer et al.

ACS Symp. Ser. (month unavailable) 1995, (Synthesis and Chemistry of Agrochemicals IV), pp. 375–383, Riordan et al.

Tetrahedron (month unavailable) 1994, vol. 50, No. 19, pp. 5741–5752, Suwinski et al.

Synlett, Apr. 1990, (5), pp. 277–278, Dudfield et al.

J. Heterocyclic Chem., Aug. 1981, pp. 997–1006, Cremlyn et al.

*Primary Examiner*—Floyd D. Higel
*Attorney, Agent, or Firm*—Joseph C. Gil; Carol Marmo

[57] ABSTRACT

The present invention concerns novel imidazol derivatives of the formula (I),

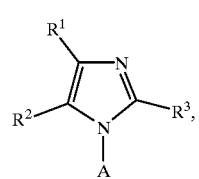

in which $R^1$, $R^2$, $R^3$ and A have the meanings given in the description, and the acid addition salts and metal salt complexes, several processes for the production of the novel substances and their use for combating undesirable microorganisms in plant and material protection.

23 Claims, No Drawings

IMIDAZOLE COMPOUNDS

This application was filed under 35 U.S.C. 371 as a national stage application of PCT/EP 97/02830 filed May 30, 1997.

TECHNICAL FIELD OF THE INVENTION

The present invention relates to novel imidazole derivatives, to a plurality of processes for their preparation and to their use as microbicides in crop protection and in the protection of materials.

BACKGROUND OF THE INVENTION

It is already known that certain imidazole derivatives have fungicidal properties (cf. EP-A 0 298 196). Thus, for example, 4-chloro-2-cyano-1-morpholine-N-ylsulphonyl-5-phenylimidazole or 4-chloro-2-cyano-5-phenyl-1-(2-thienylsulphonyl)-imidazole can be employed for controlling fungi. The activity of these substances is good, but in some cases leaves something to be desired at low application rates.

DETAILED DESCRIPTION OF THE INVENTION

This invention, accordingly, provides novel imidazole derivatives of the formula

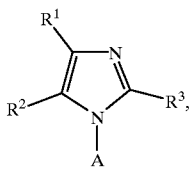

(I)

in which $R^1$ and $R^2$ are identical or different and independently of one another each represent hydrogen, halogen, cyano, thiocyanato, nitro, formyl, carboxyl, carbamoyl, thiocarbamoyl, alkyl, alkoxy, alkylthio, alkylsulphinyl, alkylsulphonyl, alkenyl, alkenyloxy, halogenoalkyl, halogenoalkoxy, halogenoalkylthio, halogenoalkylsulphinyl, halogenoalkylsulphonyl, halogenoalkenyl, halogenoalkenyloxy, alkylcarbonyl, alkylcarbonyloxy, alkoxycarbonyl, alkylsulphonyloxy, alkoxinminoalkyl, cycloalkyl, alkylamino, hydroxyalkylamino, dialkylamino, hydroximinoalkyl or represent $Z-R^4$, where Z represents alkanediyl, alkenediyl, alkinediyl, —*Q—CQ—, —*CQ—Q—, —*CH$_2$—Q—, —Q*—CH$_2$—, —*CQ—Q—CH$_2$—, —*CH$_2$—Q—CQ—, —*Q—CQ—CH$_2$—, —*Q—CQ—Q—CH$_2$—, —S(O)$_n$—, —*CH$_2$—S(O)$_n$—, —CQ— or —*S(O)$_n$—CH$_2$—, in which Q represents oxygen or sulphur and the atoms labelled with (*) are in each case attached to $R^4$, n represents 0, 1 or 2 and $R^4$ represents optionally substituted aryl or optionally substituted heterocyclyl, or Z represents a direct bond or represents an oxygen atom and $R^4$ represents optionally substituted aryl, $R^3$ represents halogen, cyano, nitro, trifluoromethyl, thiocarbamoyl, thiocyanato or the grouping

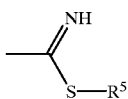

in which $R^5$ represents alkyl,

A represents a grouping of the formula —SO$_2$—R$^6$ or

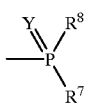

in which

Y represents oxygen or sulphur and $R^6$ represents an optionally substituted, unsaturated heterocyclic radical which contains at least one nitrogen or oxygen atom, and $R^7$ and $R^8$ independently of one another each represent alkyl, halogenoalkyl, alkoxy, halogenoalkoxy, alkylthio, halogenoalkylthio, alkenyl, halogenoalkenyl, alkenyloxy, alkenylthio, alkinyl, alkinyloxy, alkinylthio, amino which is optionally substituted by alkyl, cycloalkyl or aryl, optionally substituted aryl, optionally substituted aryloxy, optionally substituted arylthio, optionally substituted cycloalkyl, optionally substituted cycloalkyloxy, optionally substituted cycloalkylthio, optionally substituted cycloalkylamnino or represent an optionally substituted, saturated or unsaturated heterocyclic radical, or $R^7$ and $R^8$ together with the phosphorus atom to which they are attached represent an optionally substituted heterocyclic radical, and also their acid addition salts and metal salt complexes.

In the definitions, the saturated or unsaturated hydrocarbon chains, such as alkyl, alkenyl or alkinyl, are in each case straight-chain or branched, including in combination with hetero atoms, such as in alkoxy, alkylthio or alkylamino.

Furthermore, it has been found that imidazole derivatives of the formula (I) and also their acid addition salts and metal salt complexes are obtained when a) imidazoles of the formula

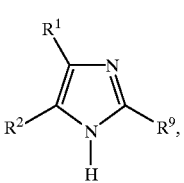

(II)

in which $R^1$ and $R^2$ are each as defined above and $R^9$ represents halogen, cyano, nitro, trifluoromethyl or thiocyanato are reacted with halides of the formula

A—X$^1$ (III)

in which

A is as defined above and $X^1$ represents halogen, if appropriate in the presence of an acid binder and if appropriate in the presence of a diluent, or when b) cyanoimidazoles of the formula

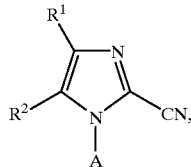

(Ia)

in which

R¹, R² and A are each as defined above are reacted with hydrogen sulphide, if appropriate in the presence of a base and if appropriate in the presence of a diluent, or when c) thiocarbamoylimidazoles of the formula

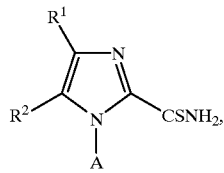

(Ib)

in which

R¹, R² and A are each as defined above are reacted with alkylating agents of the formula $$R^5-X^2 \quad \quad (IV)$$

in which

R⁵ is as defined above and

X² represents a leaving group, if appropriate in the presence of an acid binder and if appropriate in the presence of a diluent, and, if appropriate, an acid or a metal salt is added to the resulting compounds of the formula (I).

Finally, it has been found that the imidazole derivatives of the formula (I) and also their acid addition salts and metal salt complexes have very good microbicidal properties and can be employed both in crop protection and in the protection of materials for controlling undesirable microorganisms.

Surprisingly, the substances according to the invention have better fungicidal activity than 4-chloro-2-cyano-1-morpholine-N-ylsulphonyl-5-phenylimidazole or 4-chloro-2-cyano-5-phenyl-1-(2-thienylsulphonyl)-imidazole, which are constitutionally similar prior-art active compounds of the same direction of action.

The formula (I) provides a general definition of the substances according to the invention.

R¹ and R² are identical or different and independently of one another preferably represent hydrogen, fluorine, chlorine, bromine, iodine, cyano, thiocyanato, nitro, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroxyiminoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety, halogenoalkylcarbonyloxy having 1 to 4 carbon atoms in the halogenoalkyl group and 1 to 5 identical or different halogen atoms, alkylthio having 1 to 4 carbon atoms, alkylsulphinyl having 1 to 4 carbon atoms, alkylsulphonyl having 1 to 4 carbon atoms, alkenyl having 2 to 4 carbon atoms, alkenyloxy having 2 to 4 carbon atoms, halogenoalkylthio having 1 to 4 carbon atoms and 1 to 5 identical or different halogen atoms, halogenoalkenyl having 2 to 4 carbon atoms and 1 to 5 identical or different halogen atoms, halogenoalkyloxy having 2 to 4 carbon atoms and 1 to 5 identical or different halogen atoms, alkylsulphonyloxy having 1 to 4 carbon atoms or represents Z-R⁴.

Z preferably represents alkanediyl having 1 to 4 carbon atoms, alkenediyl having 2 to 4 carbon atoms, alkinediyl having 2 to 4 carbon atoms or a group of the formula —*Q—CQ—, —*CQ—Q—, —*CH₂—Q—, —*Q—CH₂—, —*CQ—Q—CH₂—, —*CH₂—Q—CQ—, —*Q—CQ—CH₂—, —*Q—CQ—Q—CH₂—, —S(O)ₙ—, —*CH₂—S(O)ₙ—, —CQ— or —*S(O)ₙ—CH₂—, where in each case the atoms labelled with * are attached to R⁴.

Q also preferably represents oxygen or sulphur.

n also preferably represents 0, 1 or 2.

R⁴ preferably represents phenyl or naphthyl, where each of these two radicals may be mono- to trisubstituted by identical or different substituents selected from the group consisting of halogen, cyano, nitro, formyl, carbamoyl, thiocarbamoyl, alkyl having 1 to 4 carbon atoms, alkoxy having 1 to 4 carbon atoms, alkylthio having 1 to 4 carbon atoms, alkenyl or alkenyloxy having in each case 2 to 4 carbon atoms, alkinyl or alkinyloxy having in each case 2 to 4 carbon atoms, halogenoalkyl, halogenoalkoxy or halogenoalkylthio having in each case 1 to 4 carbon atoms and 1 to 5 identical or different halogen atoms, halogenoalkenyl or halogenoalkenyloxy having in each case 2 to 4 carbon atoms and 1 to 5 identical or different halogen atoms, halogenoalkinyl or halogenoalkinyloxy having in each case 2 to 4 carbon atoms and 1 to 5 identical or different halogen atoms, alkylamino, dialkylamino, alkoxycarbonyl, hydroximinoalkyl or alkoximinoalkyl having in each case 1 to 4 carbon atoms in the individual alkyl moieties, cycloalkyl having 3 to 6 carbon atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylcarbonyl having 1 to 4 carbon atoms in the alkyl group, alkylcarbonyloxy having 1 to 4 carbon atoms in the alkyl moiety and alkylsulphonyloxy having 1 to 4 carbon atoms, or else may be monosubstituted by doubly attached dioxyalkylene having 1 or 2 carbon atoms which may optionally be mono- to tetrasubstituted by identical or different halogens, where the oxygen atoms are not adjacent.

$R^4$ additionally preferably represents an unsaturated heterocyclyl radical having 5 or 6 ring members and 1 to 3 hetero atoms, such as nitrogen, oxygen and/or sulphur, where these radicals may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 3 carbon atoms in the alkoxy moiety, cycloalkyl having 3 to 6 carbon atoms, cyano and nitro.

Z additionally also preferably represents a direct bond or represents an oxygen atom if $R^4$ represents phenyl or naphthyl, where each of these two radicals may be mono- to trisubstituted by identical or different substituents selected from the group consisting of those radicals which have already been mentioned above as phenyl or naphthyl substituents.

$R^3$ preferably represents fluorine, chlorine, bromine, iodine, cyano, nitro, trifluoromethyl, thiocarbamoyl, thiocyanato or the grouping

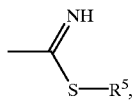

in which $R^5$ represents alkyl having 1 to 4 carbon atoms.

A also preferably represents a grouping of the formula —$SO_2$—$R^6$ or

Y also preferably represents oxygen or sulphur.

$R^6$ preferably represents an unsaturated heterocyclyl radical having 5 or 6 ring members and 1 to 3 hetero atoms, such as oxygen, sulphur and/or nitrogen, where at least one hetero atom represents nitrogen or oxygen, and where the heterocycles may be mono-, di- or else trisubstituted by identical or different substituents selected from the group consisting of halogen, cyano, nitro, hydroxyl, mercapto, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxy carbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroxyiminoalkyl having 1 to 4 carbon atoms in the alkyl moiety, alkoxyiminoalkyl having 1 to 4 carbon atoms in the alkoxy moiety and 1 to 4 carbon atoms in the alkyl moiety, alkylcarbonyloxy having 1 to 4 carbon atoms in the alkyl moiety, halogenoalkylcarbonyloxy having 1 to 4 carbon atoms in the halogenoalkyl group and 1 to 5 identical or different halogen atoms, alkylthio having 1 to 4 carbon atoms, alkylsulphinyl having 1 to 4 carbon atoms, alkylsulphonyl having 1 to 4 carbon atoms, halogenoalkylthio having 1 to 4 carbon atoms and 1 to 5 identical or different halogen atoms, alkylsulphonyloxy having 1 to 4 carbon atoms, or by pyrrolidinyl, piperidinyl, piperidyl, morpholinyl or piperazinyl, each of which is optionally mono- or disubstituted by methyl, $R^7$ and $R^8$ independently of one another each preferably represent straight-chain or branched alkyl having 1 to 4 carbon atoms, straight-chain or branched halogenoalkyl having 1 to 4 carbon atoms and 1 to 5 identical or different halogen atoms, straight-chain or branched alkoxy having 1 to 4 carbon atoms, straight-chain or branched halogenoalkoxy having 1 to 4 carbon atoms and 1 to 5 identical or different halogen atoms, straight-chain or branched alkylthio having 1 to 4 carbon atoms, straight-chain or branched halogenoalkylthio having 1 to 4 carbon atoms and 1 to 5 identical or different halogen atoms, straight-chain or branched alkenyl having 2 to 4 carbon atoms, straight-chain or branched halogenoalkenyl having 2 to 4 carbon atoms and 1 to 5 identical or different halogen atoms, straight-chain or branched alkenyloxy having 2 to 4 carbon atoms, straight-chain or branched alkenylthio having 2 to 4 carbon atoms, straight-chain or branched alkinyl having 2 to 4 carbon atoms, straight-chain or branched alkinyloxy having 2 to 4 carbon atoms, straight-chain or branched alkinylthio having 2 to 4 carbon atoms, amino which is optionally mono- or disubstituted by identical or different substituents selected from the group consisting of alkyl having 1 to 4 carbon atoms, cycloalkyl having 3 to 7 carbon atoms, or phenyl, or represents phenyl, phenoxy, phenylamino or phenylthio, where each of these radicals may be mono- to trisubstituted by identical or different substituents selected from the group consisting of fluorine, chlorine, bromine, alkyl having 1 to 4 carbon atoms, halogenoalkyl having 1 to 4 carbon atoms and 1 to 5 fluorine, chlorine and/or bromine atoms, alkoxy having 1 to 4 carbon atoms and halogenoalkoxy having 1 to 4 carbon atoms and 1 to 5 fluorine, chlorine and/or bromine atoms, or represents cycloalkyl having 3 to 7 carbon atoms, cycloalkyloxy having 3 to 7 carbon atoms, cycloalkylthio having 3 to 7 carbon atoms, cycloalkylamino having 3 to 7 carbon atoms, where each of these abovementioned radicals may be mono- to trisubstituted by identical or different substituents selected from the group consisting of fluorine, chlorine, bromine, alkyl having 1 to 4 carbon atoms and halogenoalkyl having 1 to 4 carbon atoms and 1 to 5 fluorine, chlorine and/or bromine atoms, or represents a saturated or unsaturated heterocyclyl radical having 5 or 6 ring members and 1 to 3 heteroatoms, such as nitrogen, oxygen and/or sulphur, where each of these radicals may be mono- or disubstituted by identical or different substituents selected from the group consisting of halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroxyiminoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety, halogenoalkylcarbonyloxy having 1 to 4 carbon atoms in the halogenoalkyl group and 1 to 5 identical or different halogen atoms, alkylthio having 1 to 4 carbon atoms, alkylsulphinyl having 1 to 4 carbon atoms, alkylsulphonyl having 1 to 4 carbon atoms, halogenoalkylthio having 1 to 4 carbon atoms and 1 to 5 identical or different halogen atoms and alkylsulphonyloxy having 1 to 4 carbon atoms.

$R^7$ and $R^8$ additionally together with the linking phosphorus atom preferably represent a 5- or 6-membered heterocyclyl radical which may contain one or two further hetero atoms, such as oxygen, sulphur and/or nitrogen, and which may be mono- to trisubstituted by identical or different substituents selected from the group consisting of fluorine, chlorine, bromine, alkyl having 1 to 4 carbon atoms, alkoxy having 1 to 4 carbon atoms and halogenoalkoxy having 1 to 4 carbon atoms and 1 to 5 fluorine, chlorine and/or bromine atoms.

$R^1$ and $R^2$ independently of one another particularly preferably represent hydrogen, fluorine, chlorine, bromine, iodine, cyano, thiocyanato, nitro, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and/or ethoxyiminoethyl or represents Z-$R^4$.

Z particularly preferably represents methanediyl, 1,1-ethanediyl, 1,2-ethanediyl, 1,1-, 1,2-, 1,3- or 2,2-propanediyl, 1,1-ethenediyl, 1,2-ethenediyl, ethinediyl, —*Q—CQ—, —*CQ—Q—, —*CH$_2$—Q—, —Q*—CH$_2$—, —*CQ—Q—CH$_2$—, —*CH$_2$—Q—CQ—, —*Q—CQ—CH$_2$—, —*Q—CQ—Q—CH$_2$—, —S(O)$_n$—, —*CH$_2$—S(O)$_n$—, —CQ— or —*S(O)$_n$—CH$_2$—, where in each case the atoms labelled with * are attached to $R^4$.

Q also particularly preferably represents oxygen or sulphur.

n also particularly preferably represents 0, 1 or 2.

$R^4$ particularly preferably represents phenyl or naphthyl, where each of these radicals may be mono- to trisubstituted by identical or different substituents selected from the group consisting of fluorine, chlorine, bromine, cyano, nitro, formyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, cyclopropyl, cyclobutyl, cyclopentyl and cyclohexyl, or else may be monosubstituted by doubly attached methylenedioxy or ethylenedioxy, each of which may optionally be mono- to tetrasubstituted by fluorine and/or chlorine.

$R^4$ furthermore particularly preferably represents an unsaturated heterocyclyl radical having 5 or 6 ring members and 1 to 3 hetero atoms, such as nitrogen, oxygen and/or sulphur, where each of these radicals may be mono- or disubstituted by identical or different substituents selected from the group consisting of fluorine, chlorine, bromine, methyl, ethyl, methoxy, ethoxy, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, methoxycarbonyl, ethoxycarbonyl, cycloalkyl having 3 to 6 carbon atoms, cyano and nitro.

Z additionally also particularly preferably represents a direct bond or represents an oxygen atom if $R^4$ represents phenyl or naphthyl, where each of these radicals may be mono- to trisubstituted by identical or different substituents selected from the group consisting of those radicals which have already been mentioned above as being particularly preferred substituents at the phenyl or naphthyl radical.

$R^3$ particularly preferably represents fluorine, chlorine, bromine, iodine, cyano, nitro, trifluoromethyl, thiocarbamoyl, thiocyanato or the grouping

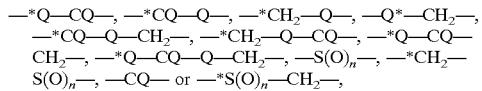

in which $R^5$ represents methyl or ethyl.

A also particularly preferably represents a grouping of the formula —SO$_2$—$R^6$ or

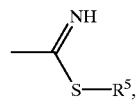

Y also particularly preferably represents oxygen or sulphur.

$R^6$ particularly preferably represents pyrrolyl, furyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridyl, pyrimidyl, pyrazinyl or pyridazinyl, where these radicals may be mono-, di- or trisubstituted by identical or different substituents selected from the group consisting of fluorine, chlorine, bromine, cyano, nitro, amino, hydroxyl, mercapto, formyl, carboxyl, carbamoyl, thiocarbamoyl, methyl, ethyl, n- or i-propyl , n-, i-, s- or t-butyl, cyclopropyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl, ethoxyiminoethyl, or by pyrrolidinyl, piperidyl, morpholinyl or piperazinyl, each of which is optionally mono- or disubstituted by methyl.

$R^7$ and $R^8$ independently of one another in particular represent methyl, ethyl, n- or i-propyl, n-, i-, s- or t-butyl, trifluoromethyl, trifluoroethyl, methoxy, ethoxy, n- or i-propoxy, n-, i-, s- or t-butoxy, difluoromethoxy, trifluoromethoxy, difluorochloromethoxy, trifluoroethoxy, methylthio, ethylthio, n- or i-propylthio, difluoromethylthio, trifluoromethylthio, difluorochloromethylthio, allyl, n- or s-butenyl; allyloxy, n- or s-butenyloxy; allylthio, n- or s-butenylthio; propargyl, n- or s-butinyl; propargyloxy; propargylthio; amino; methylamino, ethylamino, n- or i-propylamnino, n-, i-, s- or t-butylamino; dimethylamino, diethylamino, di-n- or di-i-propylamino, methylethylamino, methyl-n-propylamino, methyl-i-propylamino, cyclopropylamino, phenylamino or methyl-phenylamino, represent phenyl, phenoxy, or phenylthio, where each of these radicals may be mono- to trisubstituted by identical or different substituents selected from the group consisting of fluorine, chlorine, bromine, methyl, ethyl, n- or i-propyl, methoxy, ethoxy, n- or i-propoxy, trifluoromethyl and trifluoromethoxy; or represent cyclopropyl, cyclopentyl, cyclohexyl, cyclopropyloxy, cyclopentyloxy, cyclohexyloxy, cyclopropylthio, cyclopentylthio, cyclohexylthio, cyclopropylamino, cyclopentylamino, cyclohexylamino, where each of these radicals may be mono- to trisubstituted by identical or different substituents selected from the group consisting of fluorine, chlorine, bromine, methyl, ethyl, n- or i-propyl and trifluoromethyl, represent pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridyl, pyrimidyl, pyrazinyl or pyridazinyl, where each of these radicals may be mono- or disubstituted by identical or different substituents selected from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and ethoxyiminoethyl, or represent pyrrolidinyl, piperidinyl, morpholinyl or piperazinyl, where each of these radicals may be mono- or disubstituted by methyl.

$R^7$ and $R^8$ additionally together with the linking phosphorus atom particularly preferably represent a 5- or 6-membered heterocyclyl radical which may contain one or two further hetero atoms, such as oxygen, sulphur and/or nitrogen, and which may be mono- to trisubstituted by identical or different substituents selected from the group consisting of methyl, ethyl, n- or i-propyl, methoxy, ethoxy, n- or i-propoxy, chlorine and trifluoromethyl.

Preferred compounds according to the invention are also the addition products of acids and those imidazole derivatives of the formula (I) in which $R^1$, $R^2$, $R^3$ and A each have the meanings which have been mentioned as being preferred for these radicals.

The acids which can be added preferably include hydrohalic acids, such as, for example, hydrochloric acid and hydrobromic acid, in particular hydrochloric acid, furthermore phosphoric acid, sulphuric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalene disulphonic acid, saccharin and thiosaccharin.

Preferred compounds according to the invention are additionally addition products of salts of metals of main groups II to IV and subgroups I, II and IV to VIII of the Periodic Table of the Elements and those imidazole derivatives of the formula (I) in which $R^1$, $R^2$, $R^3$ and A each have those meanings which have been mentioned as being preferred for these radicals.

Particular preference here is given to the salts of copper, zinc, manganese, magnesium, tin, iron and nickel. Suitable anions of these salts are those which are derived from those acids which lead to physiologically acceptable addition products. Particularly preferred acids of this kind are, in this context, the hydrohalic acids, such as, for example, hydrochloric acid and hydrobromic acid, furthermore phosphoric acid, nitric acid and sulphuric acid.

Examples of substances according to the invention which may be mentioned are the imidazole derivatives listed in Tables 1 to 13 below:

TABLE 1

(I-c)

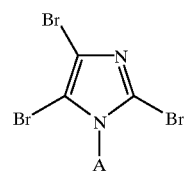

where A represents the following substituents:

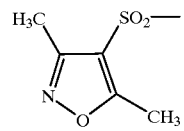

TABLE 1-continued
(I-c)
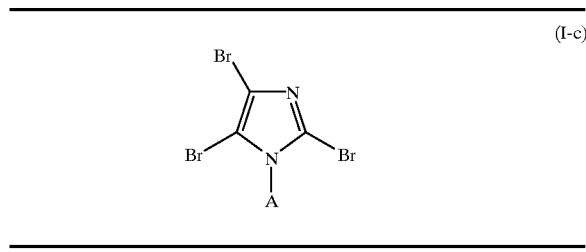
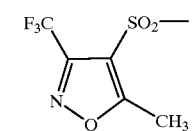
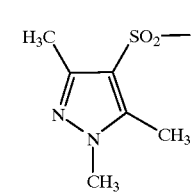
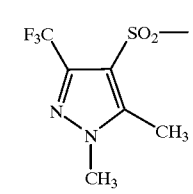
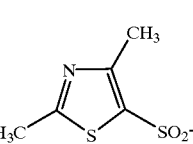
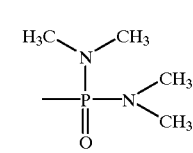
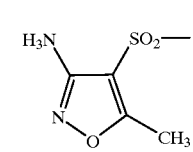
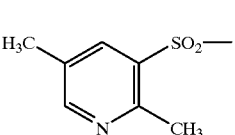
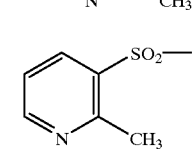
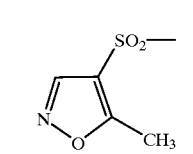
TABLE 1-continued
(I-c)
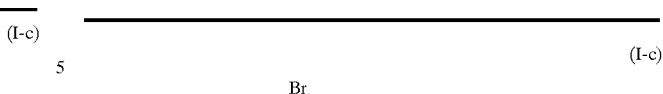
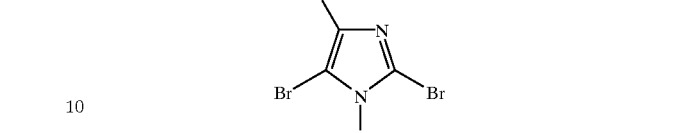
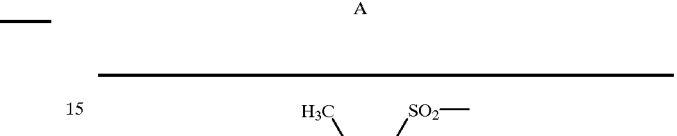
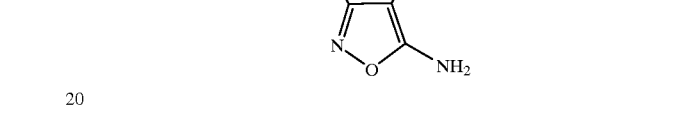
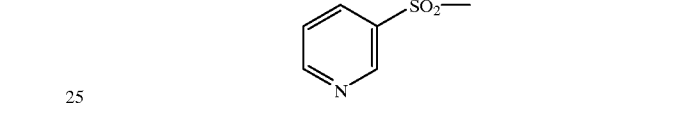
TABLE 2
(I-d)
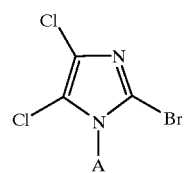
where A represents the substituents mentioned in Table 1.
TABLE 3
(I-e)
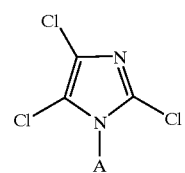
where A represents the substituents mentioned in Table 1.

TABLE 4

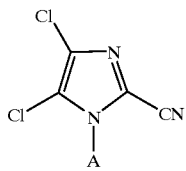
(I-f)

where A represents the substituents mentioned in Table 1.

TABLE 5

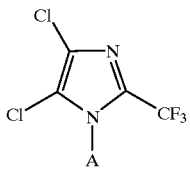
(I-g)

where A represents the substituents mentioned in Table 1.

TABLE 6

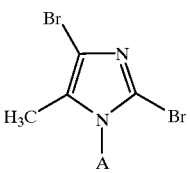
(I-h)

where A represents the substituents mentioned in Table 1.

TABLE 7

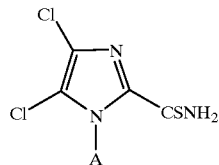
(I-i)

where A represents the substituents mentioned in Table 1.

TABLE 8

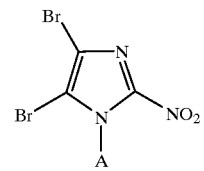
(I-k)

where A represents the substituents mentioned in Table 1.

TABLE 9

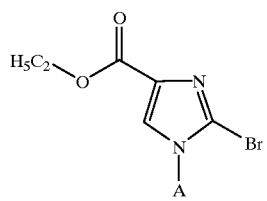
(I-l)

where A represents the substituents mentioned in Table 1.

TABLE 10

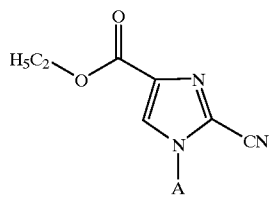
(I-m)

where A represents the substituents mentioned in Table 1.

TABLE 11

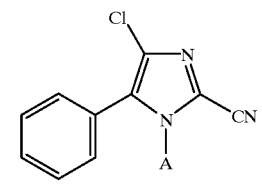
(I-n)

where A represents the substituents mentioned in Table 1.

TABLE 12

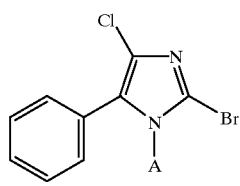
(I-o)

where A represents the substituents mentioned in Table 1.

TABLE 13

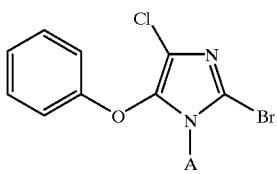
(I-p)

where A represents the substituents mentioned in Table 1.

Using 2,4,5-tribromoimidazole and furan-2-sulphonyl chloride as starting materials, the course of step (a) of the process according to the invention can be illustrated by the following equation:

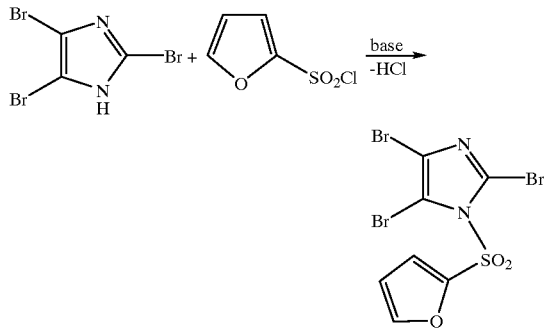

Using 4-chloro-2-cyano-1-(2-furyl-sulphonyl)-5-phenylimidazole as starting materials and hydrogen sulphide as reaction component, the course of step (b) of the process according to the invention can be illustrated by the following equation:

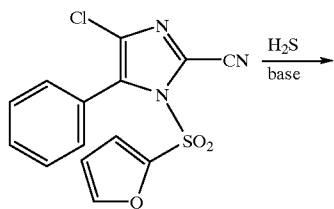

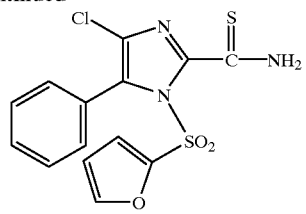

Using 4-chloro-1-(2-furyl-sulphonyl)-5-phenyl-imidazole-2-thiocarbamide as starting material and iodomethane as reaction component, the course of the step (c) of the process according to the invention can be illustrated by the following equation:

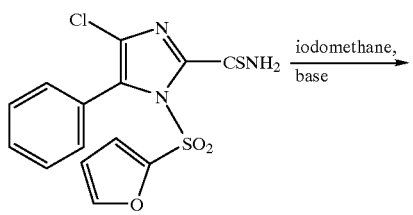

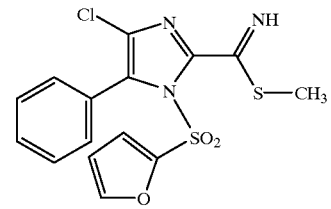

The formula (II) provides a general definition of the imidazoles required as starting materials for carrying out step (a) of the process according to the invention. In this formula, $R^1$ and $R^2$ preferably have those meanings which have already been mentioned in connection with the description of the substances of the formula (I) according to the invention as being preferred for these radicals. $R^9$ preferably represents fluorine, chlorine, bromine, iodine, cyano, nitro or thiocyanato.

The imidazoles of the formula (II) are known or can be prepared by known methods (cf. Chem. Ber. (1877) 10, 1370; J. Heterocycl. Chem. (1967) 4, 399; Chem. Ber. (1976) 109, 1625; DE-A 2634053; DE-A 2646192; J. Chem. Soc. (1910) 97, 1824; J. Chem. Soc. Perkin Trans. 1 (1989) 95–99; ACS Symp. Ser. (95), 584 (Synthesis and Chemistry of Agrochemicals IV), 375–83; Tetrahedron (1994), 50(19), 5741–52; EP-A 0390506; Synlett (1990), (5), 277–8; WO 95-17390; EP-A 0298196).

The formula (III) provides a general definition of the halides required as reaction components for carrying out the step (a) of the process according to the invention. In this formula, A preferably has those meanings which have already been mentioned in connection with the description of the substances of the formula (I) according to the invention as being preferred for this substituent.

$X^1$ preferably represents chlorine or bromine.

The halides of the formula (III) are known or can be prepared by known methods (cf. J. Heterocyclic Chem. 1981, 997–1006).

Step (a) of the process according to the invention is preferably carried out in the presence of an acid binder. Suitable acid binders are all customary inorganic and organic bases. Preference is given to using alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, further ammonium compounds, such as ammonium hydroxide, ammonium acetate or ammonium carbonate, and furthermore tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the step (a) of the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, nor i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; sulphones, such as sulpholane, or amines, such as pyridine.

When carrying out the step (a) of the process according to the invention, the reaction temperatures can be varied within a relatively wide range. In general, the reaction is carried out at temperatures between 0 and 150° C., preferably at temperatures between 20 and 120° C.

Both step (a) and steps (b) and (c) of the process according to the invention are generally carried out under atmospheric pressure. However, it is also possible to operate under elevated or reduced pressure.

When carrying out the step (a) of the process according to the invention, generally 1 to 15 mol, preferably 1 to 2 mol, particularly preferably 1 to 1.3 mol of halide of the formula (III) are employed per mole of imidazole of the formula (II). Work-up is carried out by customary methods. In general, the reaction mixture is diluted with water and then extracted with an organic solvent which is only sparingly miscible with water, the combined organic phases are dried and concentrated under reduced pressure. The product that remains can be freed of any impurities that may still be present using customary methods, such as chromatography or recrystallization. If the reaction is carried out in a water-miscible organic solvent, the desired product is sometimes obtained as a solid when the reaction mixture is diluted with water. In these cases, an extraction is unnecessary. Rather, the solid is separated off and, if appropriate, purified by customary methods.

The formula (Ia) provides a general definition of the cyanoimidazoles required as starting materials for carrying out the step (b) of the process according to the invention. These are substances according to the invention which can be prepared by reactions in accordance with step (a) of the process according to the invention.

Suitable bases for carrying out step (b) of the process according to the invention are all customary inorganic and organic acid binders. Preference is given to using those acid acceptors which have already been mentioned in connection with the description of step (a) of the process according to the invention as being preferred acid binders.

Suitable diluents for carrying out the step (b) of the process according to the invention are water and also all customary inert organic solvents. Preference is given to using optionally halogenated aliphatic, alicyclic or aromatic hydrocarbons, such as, for example, petroleum ether, hexane, heptane, cyclohexane, methylcyclohexane, benzene, toluene, xylene, decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxy ethane, 1,2-diethoxyethane or anisol; amides, such as N,N-dimethylformamide; N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; amines, such as pyridine; alcohols, such as methanol, ethanol, n- or i-propanol, n, i-, sec- or tert-butanol, ethanediol, propane- 1,2-diol, ethoxyethanol, methoxyethanol, diethylene glycol monomethyl ether, diethylene glycol monoethyl ether, mixtures thereof with water or pure water.

When carrying out the step (b) of the process according to the invention, the reaction temperatures can also be varied within a relatively wide range. In general, the reaction is carried out at temperatures of between 0° C. and 150° C., preferably between 20° C. and 120° C.

When carrying out the step (b) of the process according to the invention, generally 1 to 1000 mol, preferably 1 to 50 mol, of hydrogen sulphide are employed per mole of cyanoimidazole of formula (Ia). Work-up is carried out by customary methods. In general, the reaction mixture is diluted with water, then extracted with an organic solvent which is only sparingly miscible [lacuna], the combined organic phases are dried and concentrated under reduced pressure. The product that remains can be freed of any impurities that may still be present using customary methods, such as chromatography or recrystallization.

The formula (Ib) provides a general definition of the thiocarbamoylimidazoles required as starting materials for carrying out step (c) of the process according to the invention.

These are substances according to the invention which can be prepared by reactions in accordance with step (b) of the process according to the invention.

The formula (IV) provides a general definition of the alkylating agents required as reaction components for carrying out step (c) of the process according to the invention. In this formula, $R^5$ preferably has those meanings which have already been mentioned in connection with the description of the substances of the formula (I) according to the invention as being preferred for this radical. $X^2$ preferably represents chlorine, bromine, iodine, methylsulphonyloxy, tolylsulphonyloxy or a radical of the formula $R^5$—O—$SO_2$—O— or $R^5$—O—CO—O—, in which $R^5$ has the abovementioned preferred meanings.

Suitable acid binders for carrying out step (c) of the process according to the invention are all customary inorganic and organic bases. Preference is given to using those acid acceptors which have already been mentioned in connection with the description of the step (a) of the process according to the invention as being preferred acid binders.

Suitable diluents for carrying out step (c) of the process according to the invention are all customary inert organic solvents. Preference is given to using those diluents which have already been mentioned in connection with step (a) of the process according to the invention as being preferred solvents for use.

When carrying out the step (c) of the process according to the invention, the reaction temperatures can also be varied within a relatively wide range. In general, the reaction is carried out at temperatures between 0° C. and 150° C., preferably between 20! C and 120° C.

When carrying out step (c) of the process according to the invention, generally 1 to 10 mol, preferably 1 to 5 mol, of an alkylating agent of the formula (IV) are employed per mole of thiocarbamoylimidazole of the formula (Ib). Work-up is again carried out by customary methods.

The imidazole derivatives of the formula (I) can be converted into acid addition salts or metal salt complexes.

For preparing acid addition salts of the compounds of the formula (I), preference is given to those acids which have already been mentioned in connection with the description of the acid addition salts according to the invention as being preferred acids.

The acid addition salts of the compounds of the formula (I) can be obtained in a simple manner by customary methods of forming salts, for example by dissolving a compound of the formula (I) in a suitable inert solvent and addition of the acid, for example hydrochloric acid, and, in a known manner, for example by filtering off, can be isolated and can be purified, if appropriate, by washing with an inert organic solvent.

For preparing metal salt complexes of the compounds of the formula (I), preference is given to using those salts of metals which have already been mentioned in connection with the description of the metal salt complexes according to the invention as being preferred metal salts.

The metal salt complexes of the compounds of the formula (I) can be obtained in a simple manner by customary processes, such as, for example, by dissolving the metal salt in alcohol, for example ethanol, and adding it to compounds of the formula (I). Metal salt complexes can be purified in a known manner, for example by filtering off, isolation and, if appropriate, by recrystallization.

The compounds according to the invention have a potent microbicidal activity and can be employed for controlling undesirable microorganisms, such as fungi and bacteria, in crop protection and in the protection of materials.

Fungicides are employed crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture and fruit and vegetable growing, such as, for example, against Venturia species, Podosphaera species, Phytophtora species and Plasmopara species. Rice diseases, such as, for example, Pyricularia species, are also controlled successfully.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extruder used is water, it is also possible to employ, for example, organic solvents as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins, and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticdiin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imnibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, nildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procyrridone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamnide, thiophanate-methyl, thiram, tioxymid, toiclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

2',6'-dibromo-2-methyl-4'-trifluoromethoxy-4'-trifluoromethyl-1,3-thiazole-5-carboxanilide, 2,6-dichloro-N-(4-trifluoromethylbenzyl)-benzamide, 2-aminobutane, 2-phenylphenol (OPP), 8-hydroxyquinoline sulphate, cis-1-(4-chlorophenyl)-2-(1H-1,2,4-triazol-1-yl)-cycloheptanol, (5RS,6RS)-6-hydroxy-2,2,7,7-tetramethyl-5-(1H-1,2,4-triazol-1-yl)-3-octanone, α-(2,4-dichlorophenyl)-β-methoxy-α-methyl-1H-1,2,4-triazole-1-ethanol, α-(1,1-dimethylethyl)-β-(2-phenoxyethyl)-1H-1,2,4-triazole-1-ethanol, 1-[1-[2-[(2,4-dichlorophenyl)-methoxy]-phenyl]-ethenyl]-1H-imidazole, bis-(1-methylethyl)-3-methyl-4-[(3-methylbenzoyl)oxy]-2,5-thiophenedicarboxylate, 2,6-dichloro-N-[[4-(trifluoromethyl)-phenyl]-methyl]-benzamide, (E)-α-(methoxyimino)-N-methyl-2-phenoxy-phenylacetamide, 9H-xanthene-2-[(phenylamino)-carbonyl]-9-carboxylic hydrazide, O-methyl S-phenyl phenylpropylphosphoramidothioate,
N-(5-chloro-2-methylphenyl)-2-methoxy-N-(2-oxo-3-oxazolidinyl)-acetade,
1-(2,4-dichlorophenyl)-2-(1H- 1,2,4-triazol- 1-yl)ethanone-O-(phenylmethyl)-oxime,
N-(2,6-dimethylphenyl)-2-methoxy-N-(tetrahydro-2-oxo-3-thienyl)-acetamide,
cis-4-[3-[4-(1,1-dimethylpropyl)-phenyl-2-methylpropyl]-2,6-dimethyl-morpholine hydrochloride,
1-(3,5-dichlorophenyl)-3-(2-propenyl)-2,5-pyrrolidindione,
1-methyl-5-nonyl-2-(phenylmethyl)-3-pyrrolidinole,
1-[[2-(4-chlorophenyl)-3-phenyloxiranyl]-methyl]-1H- 1,2,4-triazole, methanetetrathiol, sodium salt,
2-(2,3,3-triiodo-2-propenyl)-2H-tetrazole,
N-[3-chloro-4,5-bis(2-propinyloxy)-phenyl]-N'-methoxy-methanimidamide,
α-(5-methyl-1,3-dioxan-5-yl)-β-[[4-(trifluoromethyl)-phenyl]-methylene]-1H-1,2,4-triazole-1-ethanol,
1-(2-methyl-1-naphthalenyl)-1H-pyrrol-2,5-dione,
N-(2,6-dimethylphenyl)-2-methoxy-N-(tetrahydro-2-oxo-3-furanyl)-acetamide,
3,4-dichloro-1-[4-(difluoromethoxy)-phenyl]-1H-pyrrol-2,5-dione,
N-[2,2,2-trichloro-1-[(chloroacetyl)-amino]-ethyl]-benzamide,
N-formyl-N-hydroxy-DL-alanine-sodium salt,
N-(4-cyclohexylphenyl)-1,4,5,6-tetrahydro-2-pyrimidinamine,
4-methyl-tetrazolo[1,5-a]quinazolin-5(4H)-one,
2-chloro-N-(2,6-dimethylphenyl)-N-(isothiocyanatomethyl)-acetamide,
ethyl[(4-chlorophenyl)-azo]-cyanoacetate,
N-(4-hexylphenyl)-1,4,5,6-tetrahydro-2-pyrimidinamine,
N-(2-chloro-4-nitrophenyl)-4-methyl-3-nitro-benzenesulphonamide,
methyl N-(chloroacetyl)-N-(2,6-dimethylphenyl)-DL-alaninate,
3-[2-(4-chlorophenyl)-5-ethoxy-3-isoxazolidinyl]-pyridine,
2-[(1-methylethyl)sulphonyl]-5-(trichloromethyl)-1,3,4-thiadiazole,
spiro[2H]-1-benzopyrane-2,1'(3'H)-isobenzofuran]-3'-one,
methyl N-(2,6-dimethylphenyl)-N-(5-isoxazolylcarbonyl)-DL-alaninate, potassium bicarbonate,
1-[[2-(2,4-dichlorophenyl)-1,3-dioxolan-2-yl]-methyl]-1H-imidazole,
1-[(diiodomethyl)-sulphonyl]4-methyl-benzene,
2-bromo-2-(bromomethyl)-pentanedinitrile,
2-[[6-deoxy4-O-(4-O-methyl-β-D-glycopyranosyl)-α-D-glucopyranosyl]-amino]-4-methoxy-1H-pyrrolo[2,3-d]pyrimidine-5-carbonitrile,
methyl 1-(2,3-dihydro-2,2-dimethyl-1H-inden-1-yl)-1H-imidazole-5-carboxylate,
2-chloro-N-(2,3-dihydro-1,1,3-trimethyl-1H-inden4-yl)-3-pyridinecarboxamide,
O,O-diethyl [2-(dipropylamino)-2-oxoethyl]-ethylphosphoramidothioate,
α-(2,4-dichlorophenyl)-β-fluoro-β-propyl-1H-1,2,4-triazole-1-ethanol,
3-(1,1-dimethylpropyl-1-oxo-1H-indene-2-carbonitrile,
2,6-dichloro-5-(methylthio)-4-pyrimidinyl-thiocyanate,
S-methyl 1,2,3-benzothiadiazole-7-carbothioate,
N-(6-methoxy)-3-pyridinyl)-cyclopropanecarboxamide,
3,5-dichloro-N-[cyano-[(1-methyl-2-propynyl)-oxy]-methyl]-benzamide,
4-chloro-2-cyano-N,N-dimethyl-5-(4-methylphenyl)-1H-imidazole-1-sulphonamide,
8-(1,1-dimethylethyl)-N-ethyl-N-propyl- 1,4-dioxaspiro[4.5]decane-2-methanamine,
2,2-dichloro-N-[1-(4-chlorophenyl)ethyl]-1-ethyl-3-methyl-cyclopropanecarboxamide,
N-(2,3-dichloro-4-hydroxyphenyl)-1-methyl-cyclohexanecarboxamide.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, AC 303 630, acephate, acrinathrin, alanycarb, aldicarb, alphamethrin, amitraz, avermnectin, AZ 60541, azadirachtin, azinphos A, azinphos M, azocyclotin, *Bacillus thuringiensis*, bendiocarb, benfuracarb, bensultap, betacyluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imnidacloprid, iprobenfos, isazophos, isofenphos, isoprocarb, isoxathion, ivernectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, piriricarb, pirirniphos M, pirirmiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, broadcasting, dusting, foaming, brushing-on and the like. It is further possible to apply the active compounds by the ultra-low volume method or to inject the preparation of active compound, or the active compound itself, into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

In some cases, the active compounds according to the invention also have herbicidal properties.

The preparation and the use of the active compounds according to the invention are illustrated by the examples below.

PREPARATION EXAMPLES

Example 1

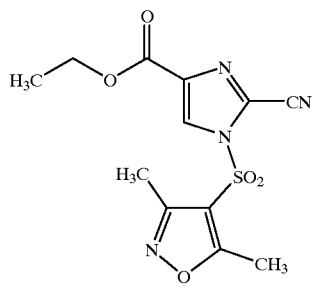
(I-1)

A solution of 2.5 g (15 mmol) of ethyl 2-cyanoimidazole4-carboxylate in 40 ml of absolute tetrahdrofuran is admixed with 0.6 g (15 mmol) of sodium hydride (60% strength suspension in mineral oil) and stirred at 20° C. for 10 minutes. 3.0 g (15 mmol) of 3,5-dimethylisoxazol-4-sulphonyl chloride are subsequently added, and the mixture is stirred at room temperature for a further 20 hours. The reaction mixture is then diluted with 150 ml of water. The resulting mixture is extracted repeatedly with 150 ml of ethyl acetate each time. The combined organic phases are dried over sodium sulphate and then concentrated under reduced pressure. The residue that remains is chromatographed over silica gel using dichloromethane as mobile phase. The eluate is concentrated under reduced pressure, giving 1.4 g (32% of theory) of ethyl 2-cyano-1(3,5-dimethyl-isoxazol-4-yl-sulphonyl)-imlidazole-4-carboxylate in the form of a colourless solid of melting point 150 to 153° C.

Example 2

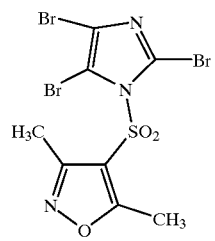
(I-2)

2.0 g (15 mmol) of potassium carbonate are added to a solution of 3.0 g (5 mmol) of 2,4,5-tribromoimidazole in 30 ml of acetonitrile, and the mixture is stirred at 20° C. for 10 minutes. 1.9 g (10 mmol) of 3,5-dimethylisoxazole-4-sulphonyl chloride are then added, and the mixture is stirred at 20° C. for 20 hours. The reaction mixture is subsequently poured into 100 ml of water. The resulting precipitate is filtered off and dried.

This gives 2.7 g (58% of theory) of 1-(3,5-dimethylisoxazol-4-yl-sulphonyl)-2,4,5tribromoimidazole in the form of a yellow solid of melting point 165 to 170° C.

Example 3

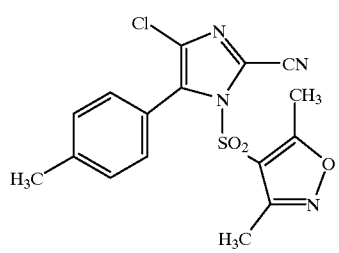
(I-3)

2.0 g (15 mmol) of potassium carbonate are added to a solution of 2.2 g (10 mmol) of 4-chloro-5-(4-tolyl)-imidazole-2-carbonitrile in 30 ml of acetonitrile, and the mixture is stirred at 20° C. for 10 minutes. The mixture is subsequently admixed with 1.9 g (10 mmol) of 3,5-dimethylisoxazole-4-sulphonyl chloride and stirred at 20° C. for 4 hours. The reaction mixture is then poured into 150 ml of water and extracted with 50 ml of ethyl acetate. The combined organic phases are dried over sodium sulphate and then concentrated under reduced pressure. The residue that remains is chromatographed over silica gel using methylene chloride as mobile phase. Concentration of the eluate under reduced pressure gives 1.8 g (50% of theory) of 4-chloro-1-(3,5-dimethylisoxazol-4-yl-sulphonyl)-5-(4-tolyl)-imidazole-2-carbonitrile in the form of a colourless solid of melting point 103 to 108° C.

The substances according to the invention listed in Table 14 below are also prepared by the methods given above.

TABLE 14

(I)

| Ex. No. | R¹ | R² | R³ | A | Physical constrants |
|---|---|---|---|---|---|
| 4 | Cl | 4-methylphenyl | Br | 3-methyl-5-methyl-isoxazol-4-yl-SO₂— | m.p. 126–133° C. |
| 5 | Br | Br | Br | 3-amino-5-methyl-isoxazol-4-yl-SO₂— | m.p. 140° C. |
| 6 | Br | Br | Br | 3-methyl-5-cyclopropyl-isoxazol-4-yl-SO₂— | $^1$H NMR*: 1.33–1.44(m, 4H); 2.35(s, 3H); 2.77–2.85(m, 1H) |
| 7 | —CH₃ | Br | Br | 3-methyl-5-methyl-isoxazol-4-yl-SO₂— | m.p. 157–160° C. |
| 8 | —CH₃ | Br | Br | 3-amino-5-methyl-isoxazol-4-yl-SO₂— | m.p. 158–162° C. |
| 9 | —Cl | —Cl | —Br | 3-methyl-5-methyl-isoxazol-4-yl-SO₂— | 140–144° C. |
| 10 | —Cl | —Cl | —Br | 3-amino-5-methyl-isoxazol-4-yl-SO₂— | 157–160° C. |
| 11 | —Cl | —Cl | Br | 3-methyl-5-cyclopropyl-isoxazol-4-yl-SO₂— | 173–176° C. |
| 12 | 4-trifloromethyl-phenyl | —H | —CF₃ | 3-methyl-5-methyl-isoxazol-4-yl-SO₂— | 114–118° C. |

TABLE 14-continued
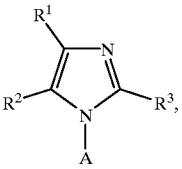
(I)
| Ex. No. | R¹ | R² | R³ | A | Physical constrants |
|---|---|---|---|---|---|
| 13 | 3,4-dichlorophenyl | —Cl | —CF₃ | 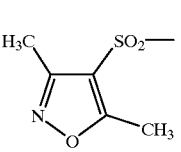 | 166–172° C. |
| 14 | 4-trifluoromethylphenyl | —H | —CF₃ | 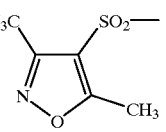 | 166–169° C. |
| 15 | —Cl | Phenyl | —Br | 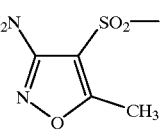 | 1H NMR=2.40*) (s, 3H); 2.82(s, 3H); 7.37–7.46(m, 3H); 7.87–7.89(m, 2H) |
| 16 | —Cl | Phenyl | —Br | 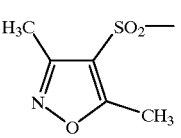 | 1H NMR=2.69*) (s, 3H); 4.85(s, 2H); 7.27–7.47(m, 3H); 7.86–7.89(m, 2H) |
| 17 | —Cl | Phenyl | —CN | 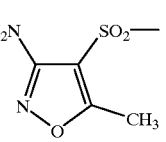 | 103–106° C. |
| 18 | —Cl | Phenyl | —CN | 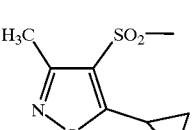 | 66–70° C. |
| 19 | —CH₃ | —Br | —Br | 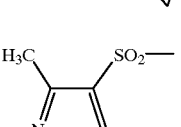 | 1H NMR=1.34–1.41*)(m, 4H); 2.27(s, 3H); 2.49 (s, 3H), 2.74–2.79 (m, 1H) |
| 20 | —CH₃ | —CH₃ | —Cl | 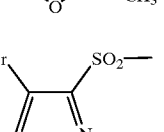 | 80–84° C. |
| 21 | —Cl | —Cl | —Br | 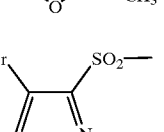 | 153–155° C. |

TABLE 14-continued

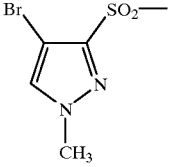

(I)

| Ex. No. | $R^1$ | $R^2$ | $R^3$ | A | Physical constrants |
|---|---|---|---|---|---|
| 22 | —CH$_3$ | —Br | —Br | 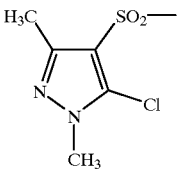 | 166–168° C. |
| 23 | —Cl | —Cl | —Br | 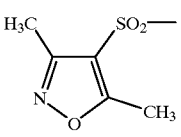 | 136–140° C. |
| 24 | —C$_2$H$_5$ | —H | —Cl | 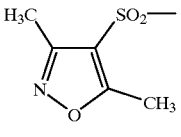 | 52–56° C. |
| 25 | —C$_2$H$_5$ | —Br | —Cl | 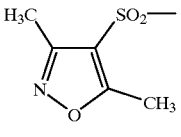 | 99–102° C. |
| 26 | -tBu | —H | —Cl | 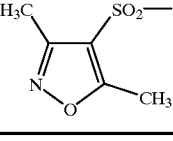 | 66–70° C. |

*) The $^1$H NMR spectra were recorded in deuterochloroform (CDCl$_3$) using tetramethylsilane (TMS) as internal standard. Stated is the chemical shift as δ value in ppm.

USE EXAMPLES

Example A

Phytophthora test (tomato)/protective
Solvent: 47 parts by weight of acetone
Emulsifier: 3 parts by weight of alkylaryl polyglycol ether To produce a suitable preparation of the active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray-coating has dried on, the plants are inoculated with an aqueous spore suspension of *Phytophthora infestans.*

The plants are placed in an incubation cabin at 100% relative atmospheric humidity and approximately 20° C.

Evaluation is carried out 3 days after the inoculation. 0% means an efficacy which corresponds to that of the untreated control, while an efficacy of 100% means that no infection is observed.

Active compounds, active compound concentrations and test results are shown in the table below.

TABLE A

Phytophthora test (tomato)/protective

| Active compound According to the invention: | Application rate of active compound in g/ha | Efficacy in % |
|---|---|---|
| 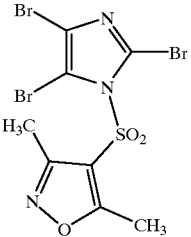 (2) | 50 | 97 |
| 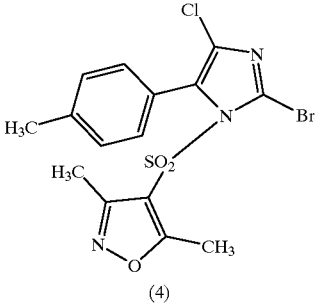 (4) | 50 | 98 |
| 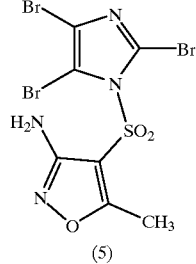 (5) | 50 | 98 |
| 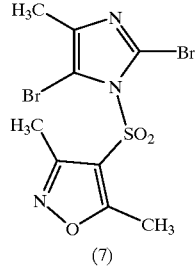 (7) | 50 | 100 |
| 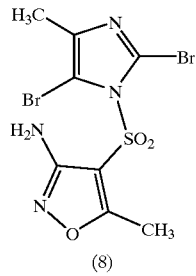 (8) | 50 | 96 |

TABLE A-continued

Phytophthora test (tomato)/protective

| Active compound According to the invention: | Application rate of active compound in g/ha | Efficacy in % |
|---|---|---|
| 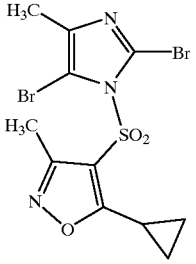 (19) | 50 | 94 |

Example B
Podosphaera test (apple)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the desired application rate. After the spray-coating has dried on, the plants are inoculated by dusting with *conidia* of the causative organism of apple mildew *Podosphaera leucotricha*.

The plants are then placed in a greenhouse at 23° C. and a relative humidity of approximately 70%.

Evaluation is carried out 10 days after the inoculation. 0% means an efficacy which corresponds to that of the untreated control, while an efficacy of 100% means that no infection is observed.

Active compounds, active compound concentrations and test results are shown in the table below.

TABLE B

Podosphera test (apple)/protective

| Active compound According to the invention: | Application rate of active compound in g/ha | Efficacy in % |
|---|---|---|
| 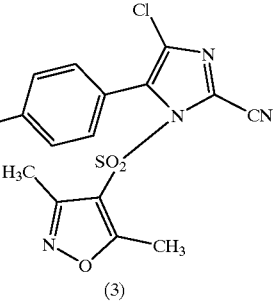 (3) | 10 | 79 |

Example C
Plasmopara test (grapevines)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray-coating has dried on, the plants are inoculated by an aqueous spore suspension of *Plasmopara viticola* and then remain in a humid chamber at 20 to 22° C. and 100% relative atmospheric humidity for 1 day. The plants are subsequently placed in a greenhouse at 21° C. and approximately 90% atmospheric humidity for 5 days. The plants are then moistened and placed in a humid chamber for 1 day.

Evaluation is carried out 6 days after the inoculation. 0% means an efficacy which corresponds to that of the untreated control, while an efficacy of 100% means that no infection is observed.

Active compounds, active compound concentrations and test results are shown in the table below.

TABLE C

Plasmopara test (grapevine)/protective

| Active compound According to the invention: | Application rate of active compound in g/ha | Efficacy in % |
|---|---|---|
| (5) | 50 | 100 |
| (4) | 50 | 99 |
| (7) | 50 | 100 |

Example D
Venturia test (apple)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray-coating has dried on, the plants are inoculated with an aqueous *conidia* suspension of the causative organism of apple scab *Venturia inaequalis* and then remain in an incubation cabin at 20° C. and 100% relative atmospheric humidity for 1 day.

The plants are then placed in a greenhouse at 20° C. and a relative atmospheric humidity of approximately 70%.

Evaluation is carried out 12 days after the inoculation. 0% means an efficacy which corresponds to that of the untreated control, while an efficacy of 100% means that no infection is observed.

Active compounds, active compound concentrations and test results are shown in the table below.

TABLE D

Venturia test (apple)/protective

| Active compound According to the invention: | Application rate of active compound in g/ha | Efficacy in % |
|---|---|---|
| (3) | 100 | 74 |
| (13) | 100 | 100 |

We claim:
1. An imidazole compound of the formula

(I)

wherein $R^1$ and $R^2$ are identical or different and independently of one another represent hydrogen, fluorine, chlorine, bromine, iodine, cyano, thiocyanato, nitro, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroxyiminoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety, halogenoalkylcarbonyloxy having 1 to 4 carbon atoms in the halogenoalkyl group and 1 to 5 identical or different halogen atoms, alkylthio having 1 to 4 carbon atoms, alkylsulphinyl having 1 to 4 carbon atoms, alkylsulphonyl having 1 to 4 carbon atoms, alkenyl having 2 to 4 carbon atoms, alkenyloxy having 2 to 4 carbon atoms, halogenoalkylthio having 1 to 4 carbon atoms and 1 to 5 identical or different halogen atoms, halogenoalkenyl having 2 to 4 carbon atoms and 1 to 5 identical or different halogen atoms, halogenoalkyloxy having 2 to 4 carbon atoms and 1 to 5 identical or different halogen atoms, alkylsulphonyloxy having 1 to 4 carbon atoms b or represents Z-R$^4$, Z represents alkanediyl having 1 to 4 carbon atoms, alkenediyl having 2 to 4 carbon atoms, alkinediyl having 2 to 4 carbon atoms or a group of the formula

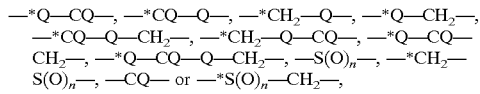

wherein in each case the atoms labeled with * are attached to R$^4$,

Q represents oxygen or sulphur, n represents 0, 1 or 2,

R$^4$ represents phenyl or naphthyl, where each of these two radicals is unsubstituted or mono- to trisubstituted by identical or different substituents selected from the group consisting of halogen, cyano, nitro, formyl, carbamoyl, thiocarbamoyl, alkyl having 1 to 4 carbon atoms, alkoxy having 1 to 4 carbon atoms, alkylthio having 1 to 4 carbon atoms, alkenyl or alkenyloxy having in each case 2 to 4 carbon atoms, alkinyl or alkinyloxy having in each case 2 to 4 carbon atoms, halogenoalkyl, halogenoalkoxy or halogenoalkylthio having in each case 1 to 4 carbon atoms and 1 to 5 identical or different halogen atoms, halogenoalkenyl or halogenoalkenyloxy having in each case 2 to 4 carbon atoms and 1 to 5 identical or different halgoen atoms, halogenoalkinyl or halogenoalkinyloxy having in each case 2 to 4 carbon atoms and 1 to 5 identical or different halogen atoms, alkylamino, dialkylamino, alkoxycarbonyl, hydroximinoalkyl or alkoximinoalkyl having in each case 1 to 4 carbon atoms in the individual alkyl moieties, cycloalkyl having 3 to 6 carbon atoms, alkysulphinyl having 1 to 4 carbon atoms, alkylsulphonyl having 1 to 4 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkycarbonyl having 1 to 4 carbon atoms in the alkyl group, alkylcarbonyloxy having 1 to 4 carbon atoms in the alkyl moiety and alkylsulphonyloxy having 1 to 4 carbon atoms, or is unsubstituted or monosubstituted by doubly attached dioxyalkylene having 1 or 2 carbon atoms which is unsubstituted or mono- to tetrasubstituted by identical or different halogens, where the oxygen atoms are not adjacent, or R$^4$ represents an unsaturated heterocyclyl radical having 5 or 6 ring members and 1 to 3 hetero atoms, selected from the group consisting of nitrogen, oxygen and sulphur, which is unsubstituted or mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 3 carbon atoms in the alkoxy moiety, cycloalkyl having 3 to 6 carbon atoms, cyano and nitro, or Z represents a direct bond or represents an oxygen atom if R$^4$ represents phenyl or naphthyl, where each of these two radicals is unsubstituted or mono- to trisubstituted by identical or different substituents selected from the group consisting of those radicals which have already been mentioned above as phenyl or naphthyl substituents, R$^3$ represents fluorine, chlorine, bromine, iodine, cyano, nitro, trifluoromethyl, thiocarbamoyl, thiocyanato or the grouping

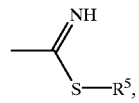

wherein

R$^5$ represents alkyl having 1 to 4 carbon atoms,

A represents a grouping of the formula —SO$_2$—R$^6$ wherein

R$^6$ represents an unsaturated heterocyclyl radical having 5 or 6 ring members and 1 to 3 hetero atoms, selected from the group consisting of oxygen, sulphur and nitrogen, where at least one hetero atom represents nitrogen or oxygen, and which is unsubstituted or mono-, di- or trisubstituted by identical or different substituents selected from the group consisting of halogen, cyano, nitro, hydroxyl, mercapto, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxy carbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroxyiminoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety, halogenoalkylcarbonyloxy having 1 to 4 carbon atoms in the halogenoalkyl group and 1 to 5 identical or different halogen atoms, alkylthio having 1 to 4 carbon atoms, alkylsulphinyl having 1 to 4 carbon atoms, alkylsulphonyl having 1 to 4 carbon atoms, halogenoalkylthio having 1 to 4 carbon atoms and 1 to 5 identical or different halogen atoms, alkylsulphonyloxy having 1 to 4 carbon atoms, or by pyrrolidinyl, piperidinyl, piperidyl, morpholinyl or piperazinyl, each of which is unsubstituted or mono- or disubstituted by methyl, or its acid salt or metal salt complex.

2. A microbicidal composition comprising a microbicidally effective amount of a compound as claimed in claim 1 and an inert diluent.

3. A method of controlling undesired microorganisms in plant protection and in the preservation of materials, which method comprises the step of applying to such undesired microorganisms or to their habitat a microbicidally effective amount of a compound as claimed in claim 1.

4. A process for preparing an imidazole compound of the formula (I) according to claim 1 comprising the step of reacting an imidazole of the formula (II)

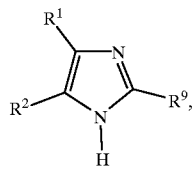

(II)

wherein $R^1$ and $R^2$ are each as defined in claim 1 and $R^9$ represents a halogen, cyano, nitro, trifluoromethyl or thiocyanato, with a halide of the formula (III)

$$A\text{—}X^1 \quad (III),$$

wherein

A is as defined in claim 1 and $X^1$ represents a halogen.

5. The process of claim 4 wherein the reaction is carried out in the presence of an acid binder or a diluent.

6. The process of claim 4 wherein the reaction is carried out in the presence of an acid binder and a diluent.

7. The process of claim 4 further comprising the step of adding an acid or a metal salt to the resulting compound of the formula (I).

8. A process for preparing an imidazole compound of the formula (I) according to claim 1 comprising the step of reacting a cyanoimidazole of the formula (Ia)

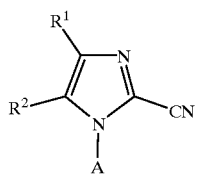

(Ia)

wherein $R^1$, $R^2$ and A are each as defined in claim 1, with hydrogen sulphide.

9. The process of claim 8 wherein the reaction is carried out in the presence of an acid binder or a diluent.

10. The process of claim 8 wherein the reaction is carried out in the presence of an acid binder and a diluent.

11. The process of claim 8 further comprising the step of adding an acid or a metal salt to the resulting compound of the formula (I).

12. A process for preparing an imidazole compound of the formula (I) according to claim 1 comprising the step of reacting a thiocarbamoylimidazole of the formula (Ib)

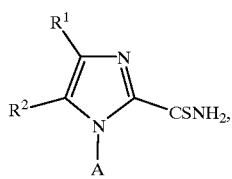

(Ib)

wherein $R^1$, $R^2$ and A are each as defined in claim 1, with an alkylating agent of the formula (IV)

$$R^5\text{—}X^2 \quad (IV)$$

wherein $R^5$ is as defined in claim 1 and $X^2$ represents a leaving group.

13. The process of claim 12 wherein the reaction is carried out in the presence of an acid binder or a diluent.

14. The process of claim 12 wherein the reaction is carried out in the presence of an acid binder and a diluent.

15. The process of claim 12 further comprising the step of adding an acid or a metal salt to the resulting compound of the formula (I).

16. An imidazole compound of the formula

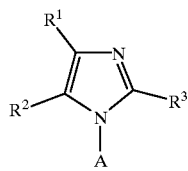

(I)

wherein $R^1$, $R^2$, $R^3$, $R^4$, $R^5$, Z, Q, n, and A are each as defined in claim. 1, and $R^6$ represents unsubstituted or substituted isoxazolyl.

17. An imidazole compound of the formula

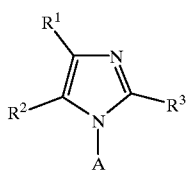
(I)

wherein
R¹, R² and R³ are each as defined in claim 1, and
A is a grouping of the formula —SO₂—R⁶,
wherein
R⁶ represents an isoxazolyl which is unsubstituted or mono- or disubstituted by a substituent selected from the group consisting of fluorine, chlorine, bromine, cyano, nitro, amino, hydroxyl, mercapto, formyl, carboxyl, carbamoyl, thiocarbamoyl, methyl, ethyl, n- or i-propyl, n-, i-, s- or t-butyl, cyclopropyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulfphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl, ethoxyiminoethyl, or by pyrrolidinyl, piperidyl, morpholinyl or piperazinyl, each of which is unsubstituted or mono- or di-substituted by methyl.

18. An imidazole compound of the formula

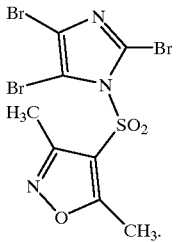

19. An imidazole compound of the formula

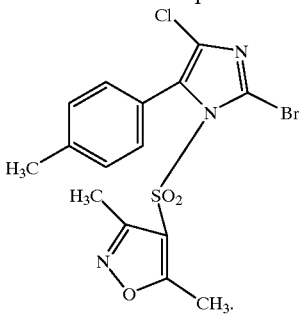

20. An imidazole compound of the formula

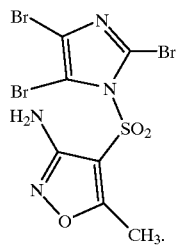

21. An imidazole compound of the formula

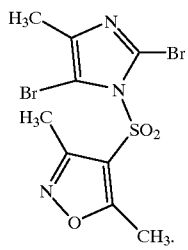

22. An imidazole compound of the formula

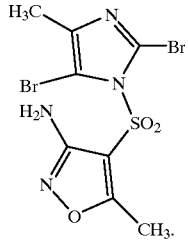

23. An imidazole compound of the formula

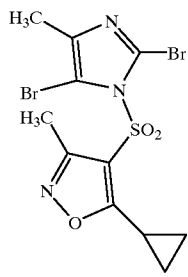

* * * * *